(12) United States Patent
Tashima et al.

(10) Patent No.: US 9,226,717 B2
(45) Date of Patent: Jan. 5, 2016

(54) HELMET-TYPE PET DEVICE

(71) Applicant: NATIONAL INSTITUTE OF RADIOLOGICAL SCIENCES, Chiba-shi, Chiba (JP)

(72) Inventors: Hideaki Tashima, Chiba (JP); Taiga Yamaya, Chiba (JP)

(73) Assignee: NATIONAL INSTITUTE OF RADIOLOGICAL SCIENCES, Chiba-shi (JP)

( * ) Notice: Subject to any disclaimer, the term of this patent is extended or adjusted under 35 U.S.C. 154(b) by 0 days.

(21) Appl. No.: 14/495,543

(22) Filed: Sep. 24, 2014

(65) Prior Publication Data

US 2015/0115162 A1 Apr. 30, 2015

(30) Foreign Application Priority Data

Oct. 30, 2013 (JP) ................................. 2013-226068

(51) Int. Cl.
*G01T 1/20* (2006.01)
*A61B 6/03* (2006.01)
*A61B 6/00* (2006.01)
*A61B 6/04* (2006.01)

(52) U.S. Cl.
CPC ................. *A61B 6/037* (2013.01); *A61B 6/501* (2013.01); *A61B 6/0478* (2013.01)

(58) Field of Classification Search
CPC ...... A61B 6/037; A61B 6/501; A61B 6/0478; G01T 1/2985
USPC ................................................... 250/363.03
See application file for complete search history.

(56) References Cited

U.S. PATENT DOCUMENTS

| 6,583,420 B1* | 6/2003 | Nelson ................ A61B 6/4233 250/363.05 |
| 8,594,404 B2 | 11/2013 | Yamaya et al. |
| 2010/0128956 A1 | 5/2010 | Yamaya et al. |
| 2014/0046180 A1 | 2/2014 | Yamaya et al. |
| 2014/0275965 A1* | 9/2014 | Majewski ............. G01T 1/2985 600/411 |

FOREIGN PATENT DOCUMENTS

| JP | A-2011-185796 | 9/2011 |
| JP | B2-4798476 | 10/2011 |
| JP | A-2012-503197 | 2/2012 |

(Continued)

OTHER PUBLICATIONS

Majewski et al., "HelmetPET: A Silicon Photomultiplier Based Wearable Brain Imager," *2011 IEEE Nuclear Science Symposium Conference Record*, 2011, pp. 4030-4034.
Yamamoto et al., "Development of a Brain PETSystem, PET-Hat: A Wearable PET System for Brain Research," *IEEE Transactions on Nuclear Science*, Jun. 3, 2011, pp. 668-673, vol. 58, No. 3.

(Continued)

*Primary Examiner* — David Porta
*Assistant Examiner* — Meenakshi Sahu
(74) *Attorney, Agent, or Firm* — Oliff PLC

(57) ABSTRACT

A helmet-type PET device includes a helmet portion (hemispherical detector) and an added portion (jaw portion detector, an ear portion detector, or a neck portion detector). The helmet portion includes a PET detector so as to cover a parietal region of an examination target. The added portion is positioned to dispose a PET detector at a part other than the parietal region of the examination target. PET measurement is performed using both an output from the PET detector at the helmet portion and an output from the PET detector at the added portion.

13 Claims, 20 Drawing Sheets

(56) References Cited

FOREIGN PATENT DOCUMENTS

| WO | WO 2008/129666 A1 | 10/2008 |
| WO | WO 2012/164664 A1 | 12/2012 |

OTHER PUBLICATIONS

Tashima et al., "A proposal of helmet PET with jaw detectors for high-sensitive brain imaging," *Journal of Nuclear Medicine*, 2013, Abstract No. 2167, vol. 54, Supplement 2.

\* cited by examiner

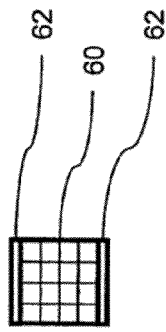
Fig. 14A BLOCK-TYPE DETECTOR
Fig. 14B MONOLITHIC BLOCK-TYPE DETECTOR
Fig. 14C PIXEL-TYPE CURVED SURFACE DETECTOR
Fig. 14D ONE-ON-ONE BASIS COUPLING
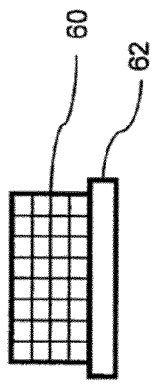
Fig. 14E DOUBLE-SIDED READING BLOCK-TYPE DETECTOR
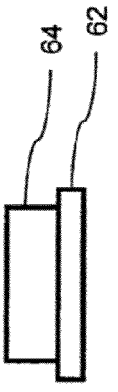
Fig. 14F MONOLITHIC-CURVED-SURFASE-TYPE DETECTOR
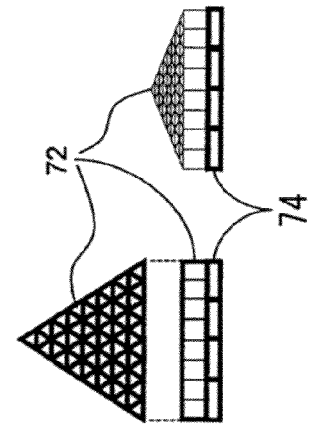
Fig. 14G TRIANGULAR-PATCH-TYPE DETECTOR

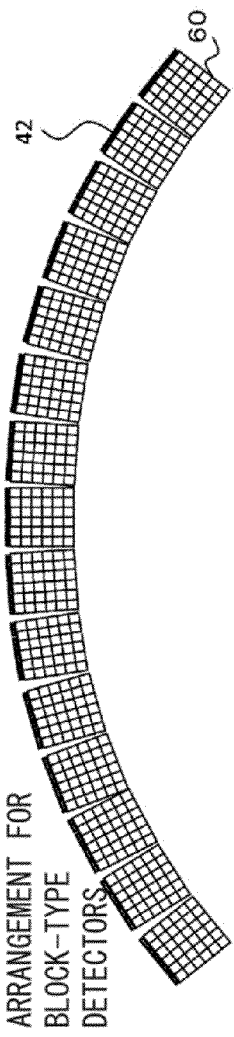
Fig. 15A ARRANGEMENT FOR BLOCK-TYPE DETECTORS
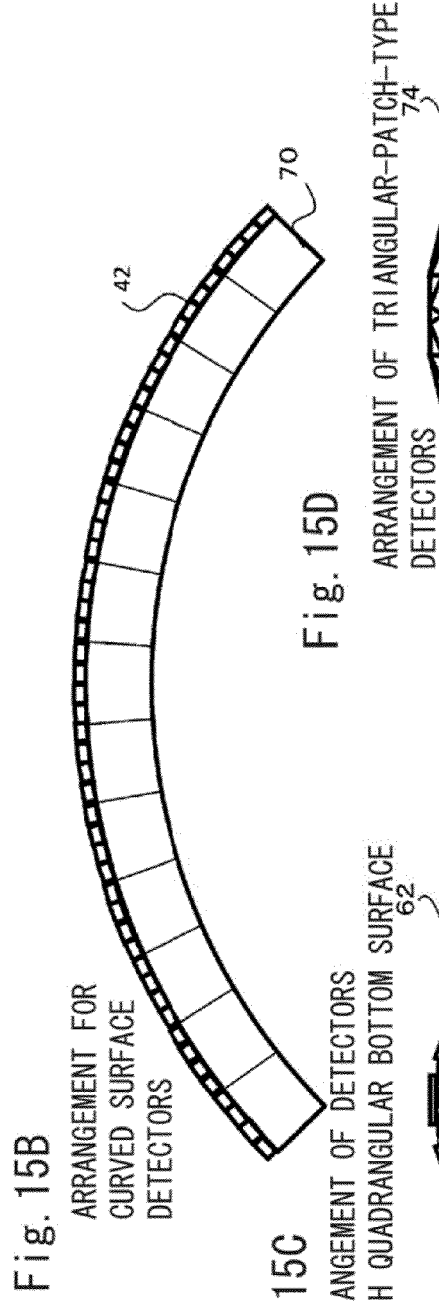
Fig. 15B ARRANGEMENT FOR CURVED SURFACE DETECTORS
Fig. 15C ARRANGEMENT OF DETECTORS WITH QUADRANGULAR BOTTOM SURFACE
Fig. 15D ARRANGEMENT OF TRIANGULAR-PATCH-TYPE DETECTORS

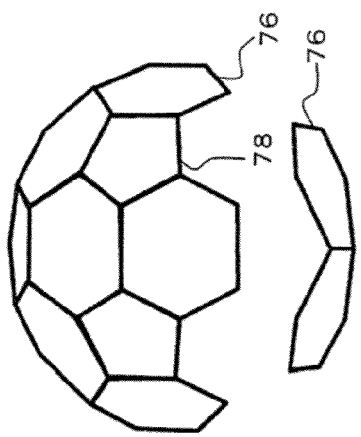
Fig. 16A HEXAGONAL DETECTOR
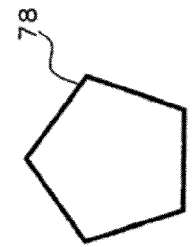
Fig. 16B PENTAGONAL DETECTOR
Fig. 16C ARRANGEMENT OF SOCCER-BALL-TYPE DETECTORS
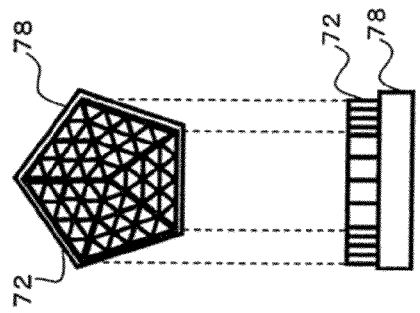
Fig. 17A HEXAGONAL DETECTOR
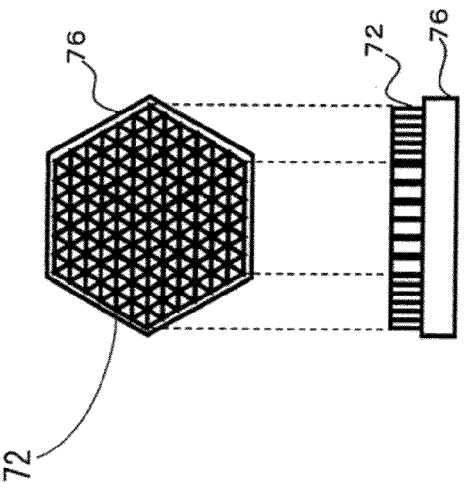
Fig. 17B PENTAGONAL DETECTOR

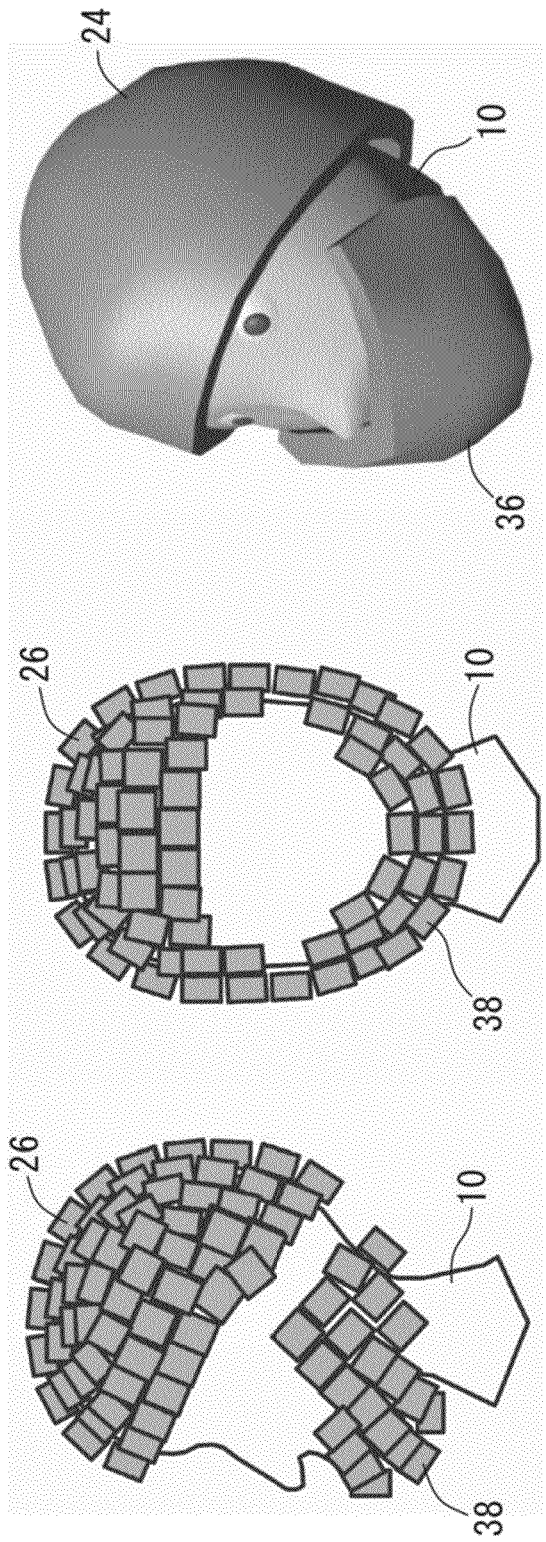

HELMET-TYPE PET DEVICE

TECHNICAL FIELD

The present invention relates to a helmet-type PET device and especially relates to a high-sensitive helmet-type PET device suitable to image brain functions.

DESCRIPTION OF THE RELATED ART

The positron emission tomography (PET) allows imaging metabolism of sugar, oxygen, or a similar element and a state of a neural receptor or a similar state as a functional image by administrating a compound labeled by an infinitesimal quantity of a positron-emitting radionuclide and detecting annihilation radiation emitted from an inside of a body. PET devices for performing this PET have been put to practical use.

In PET, a pair of radiation detectors performs coincidence counting of a pair of annihilation radiations of 511 keV generated when positrons emitted from the positron-emitting radionuclides by positron decay annihilate with surrounding electrons for measurement. This allows identifying a position where a nuclide is present on a line segment connecting the pair of detectors. Two-dimensional or three-dimensional image reconstruction method images a nuclide distribution from data measured by the plurality of detector pair.

Brain PET dedicated in measurement of brain functions is effective for early diagnosis of diseases, such as the Alzheimer's disease and the Parkinson's disease, and for investigating nervous activity. For more accurate diagnosis, obtaining images of high image quality is required. Therefore, performance required for the device includes a spatial resolution and sensitivity. Decreasing a size of elements of the detector improves the spatial resolution. The sensitivity can be improved by increasing the thickness of the detectors and also by increasing solid angles of the detectors.

To increase the measured solid angles and enhance the sensitivity of the PET device, usually, a large number of PET detectors are cylindrically disposed. However, a long, tunnel-shaped patient port increases psychological stress of the patient. Moreover, this makes examinations with a visual stimulus to the patient during measurement, or a similar stimulus difficult. In particular, depriving eyesight of a mental patient causes the patient's mental unstable due to the psychological stress, making the examination difficult.

Against this problem, the applicants have proposed an open-type PET device (also referred to as an Open PET) (Japanese Unexamined Patent Application Publication No. WO2008/129666). The open-type PET device includes a plurality of divided detector rings that are separately disposed and has field-of-view (FOV) regions that are physically open. In addition to the open-type PET device, which includes the divided detector rings, there has also been proposed an open-type PET (Japanese Unexamined Patent Application Publication No. WO2012/164664). The open-type PET is shaped like a circular cylinder that is cut by two planes inclined with respect to the sections of the circular cylinder. There has been also proposed a PET detector operable in an MRI port (Japanese Unexamined Patent Application Publication No. 2011-185796). The PET detector forms an open region in the vicinity of a visual field in a head PET device that can be configured as a PET/MRI device. From other groups, there have been also proposed systems where PET detectors disposed into a ring shape are disposed at an inside of a helmet, are mounted like a cap, or are mounted by a similar method so as to be secured to a peripheral area of a head (Japanese Unexamined Patent Application Publication No. 2012-503197, S. Majewski, et al., (2011), HelmetPET: A Silicon Photomultiplier Based Wearable Brain Imager, In 2011 IEEE Nuclear Science Symposium Conference Record (pp. 4030 to 4034), and S. Yamamoto, et al., "Development of a Brain PET system, PET-Hat: A Wearable PET System for Brain Research," IEEE Trans, Nucl. Sci., vol. 58, pp. 668 to 673, JUNE 2011).

Additionally, the applicants also have proposed a cap-shaped dosimeter fitting wear as means to dispose detectors at the peripheral area of the head (Japanese Patent No. 4798476).

However, only disposing the detectors in the helmet shape or in the cap shape has a problem that the sensitivity of a part other than the inside of the helmet or the cap is not sufficient.

The present invention has been made to solve the conventional problems. The object of the present invention is to achieve brain PET measurement where sufficient sensitivity can be obtained also at a region other than a region in the vicinity of the parietal region inside of the helmet, in particular a center portion including a cerebellum part, which is used as a reference region in the measurement of brain functions, while ensuring wide visual field. The present invention also achieves highly accurate brain PET measurement while reducing a cost of the device. Here, "a reference region in the measurement of brain functions" means a region where a molecule to which a radioactive pharmaceutical specifically binds is absent, such as a receptor to which ligand specifically binds, or a similar molecule. The reference region is employed for a method in which binding capacity is quantified without using a plasma radioactivity concentration.

SUMMARY

The present invention solves the problem with a helmet-type PET device. The helmet-type PET device includes a helmet portion and an added portion. The helmet portion includes a PET detector so as to cover a parietal region of an examination target, for example. The added portion is positioned to dispose a PET detector at a part other than the helmet portion, the parietal region of the examination target, for example. PET measurement is performed using both an output from the PET detector at the helmet portion and an output from the PET detector at the added portion.

Here, the added portion can be positioned at a front side of the helmet portion, namely a jaw of the examination target, at least one lateral side of the helmet portion, namely, an ear of the examination target, or a lower side of the helmet portion, namely, a neck of the examination target, for example.

Alternatively, the PET detector at the helmet portion and the PET detector at the added portion can be disposed on a same spherical surface.

Alternatively, the PET detector at the helmet portion and the PET detector at the added portion can be disposed close to a head of the examination target according to a shape of the examination target head, for example.

Alternatively, the helmet portion can have a shape of hemisphere.

Alternatively, the added portion can be positioned at the front side of the helmet portion with open angle $\alpha$ in horizontal direction more than 0.5 degree and less than 90 degree, preferably 60 degree, and open angle $\beta$ in vertical direction more than 0.5 degree and less than 40 degree, preferably 10 degree.

Alternatively, detector elements consisting the PET detector can have a size less than about 3 mm square.

Alternatively, the helmet portion and the added portion can be integrated into a chair.

Alternatively, the added portion can be disposed on a chin rest.

Alternatively, the helmet portion can be divided into a front portion and a rear portion, and the front portion can be supported by a pillar together with the chin rest.

Alternatively, the PET detector can be one of a block-type detector, a monolithic block-type detector, a pixel-type curved surface detector, one-to-one basis coupling-type detector, a double-sided reading block-type detector, a monolithic-curved-surface-type detector and a triangular-patch-type detector.

Alternatively, the PET detector can be constituted by hexagonal detectors and pentagonal detectors, which are arranged into a soccer ball shape.

Alternatively, the hexagonal detectors can be constituted by arranging triangular pole scintillators having a cross section of regular triangle, and the pentagonal detectors can be constituted by arranging triangular pole scintillators having a cross section of isosceles triangle.

The present invention can achieve brain PET measurement where sensitivity can be efficiently enhanced at a region other than a region in the vicinity of the parietal region inside of the helmet, in particular a center portion of a cerebellum part, which is used as a reference region in the measurement of brain functions while ensuring wide visual field. The present invention also achieves highly accurate brain PET measurement while reducing a cost of the device.

Here, a detector to be added is not necessarily to be at the jaw portion. For example, the detector is disposed at an ear position. Alternatively, the detector is disposed at a neck or a cheek position. These arrangements can achieve improvement of the sensitivity at the center portion. However, from an aspect of reconstruction of images, disposing detectors at a jaw part allows obtaining projection images in a direction perpendicular to detector elements disposed at an outer circumference of a head in a hemispherical detector. This corrects a variation in image degradation depending on directions; therefore, improvement of the image quality can be expected.

BRIEF DESCRIPTION OF THE DRAWINGS

FIGS. 14A to 14G list available configurations of the detectors;

FIGS. 15A to 15D illustrate arrangement methods for detectors;

FIGS. 16A to 16C illustrate detectors of two shapes required to achieve a soccer-ball-shaped detector, a hexagonal detector (FIG. 16A) and a pentagonal detector (FIG. 16B), and an arrangement method of the soccer-ball-shaped detector;

FIGS. 17A and 17B illustrate exemplary configurations of hexagonal detectors and pentagonal detectors arranged in a triangular pole scintillator array, respectively;

FIGS. 21A, 21B and 21C are conceptual diagrams of the forth embodiment of the present invention.

DETAILED DESCRIPTION

Figure 1:
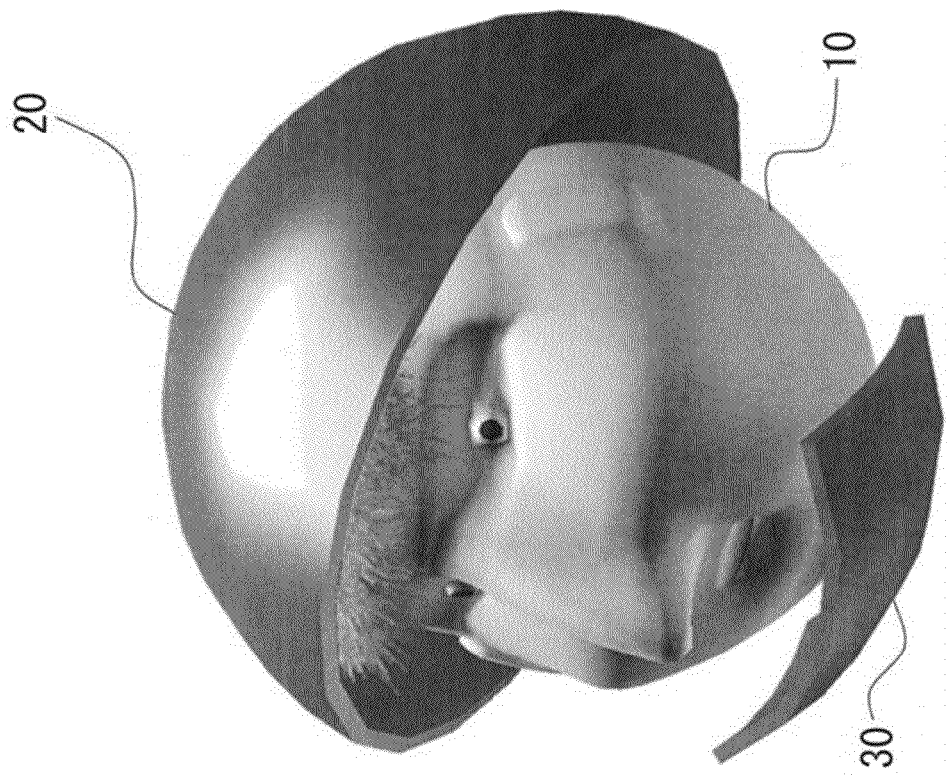
FIG. 1 illustrates a conceptual diagram of a first embodiment of the present invention.

Hereinafter, a description will be given in detail for embodiments of the present invention by referring to the drawings. The present invention is not limited by contents of the following embodiments and working examples. Also, requirements that can be easily conceived of by one skilled in the art, and a substantially identical component, or a so-called equivalent are included in the requirements of the following embodiments and working examples. Further, the components disclosed in the following embodiments and working examples may be appropriately combined or may be appropriately selected.

A first embodiment of the present invention is, as illustrated in FIG. 1, a helmet-type PET device that includes a hemispherical detector 20 and a jaw portion (a front side) detector 30. The hemispherical detector 20 is a helmet portion where PET detectors are hemispherically disposed so as to cover a parietal region of an examination target (also referred to as an examinee) 10. The jaw portion detector 30 is an added portion to dispose the PET detectors at a jaw part.

Conventionally, the PET detector has a block shape; however, the present invention assumes the use of more finely divided detector elements. Specifically, as the example illustrated in FIGS. 14C, 14D, and 14F, which will be described later, the PET detectors are achieved by disposing the detector elements finer than around 3 mm square-sized on a free curved surface at any given intervals. Alternatively, using a scintillator with curved surface that is an unpixelated detector element, a detector that estimates a detecting position of gamma ray like a monolithic detector may be employed. Alternatively, a hemispherical scintillator may be divided and be pixelated. Alternatively, the detector element may have a triangular shape so as to configure a spherical surface with triangular patches.

The size of the jaw portion detector 30 is determined considering a cost of the detector to be added and an efficiency of an increase in sensitivity. Open angle parameters $\alpha$ (corresponding to a width in a horizontal direction) and $\beta$ (corresponding to a width in a vertical direction) (see FIG. 3) determine the size of the jaw portion detector 30. Ranges of the open angle parameters $\alpha$ and $\beta$ are limited by the size of the detector element (minimum); and the size of required visual field and the size where a neck passes through (maximum). In the case where the size of the detector element is set at 1 mm and a diameter of the device is 25 cm, the range of $\alpha$ is approximately 0.5° at the minimum to 90° at the maximum and the range of $\beta$ is approximately 0.5° at the minimum to 40° at the maximum. To reduce a difference in sensitivity between a margin portion and a center portion, obtaining geometric sensitivity, providing reference regions, and comparing the sensitivity at the reference regions allows obtaining appropriate parameters. Since the difference in sensitivity does not significantly change even if an increased amount of the detector exceeds 10%, approximately of $\alpha=60°$ and $\beta=10°$ are preferred.

Figure 2:
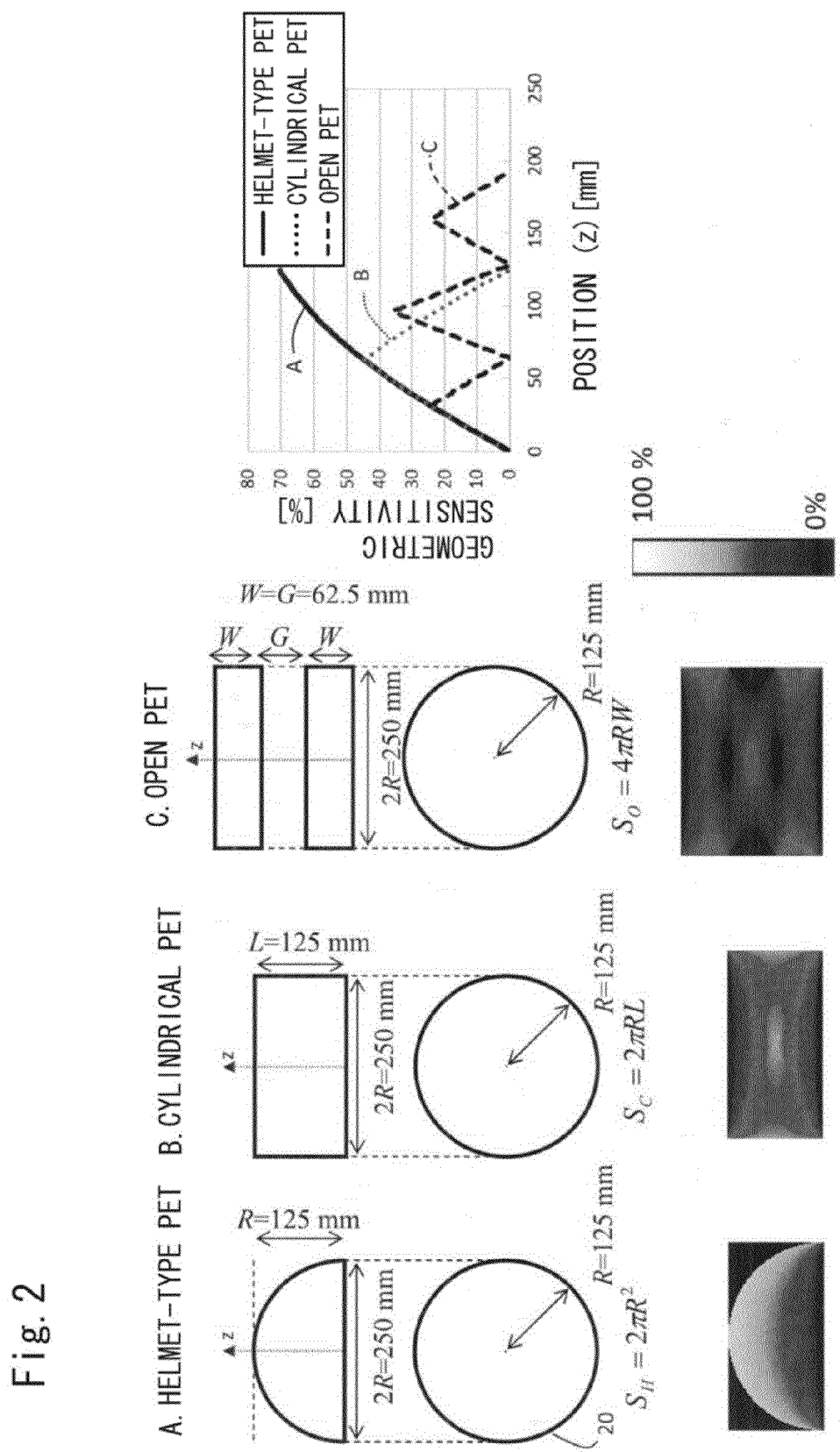
FIG. 2 illustrates a helmet-type PET device configured of only hemispherical detector, a cylindrical PET device, an Open PET device, which is an open-type PET device, each configured so as to be the same detector surface area, and a graph that compares sensitivity distributions of the helmet-type PET device, the cylindrical PET device, and the Open PET device.

First, the following describes features of excellent sensitivity of a helmet-type PET device constituted only with a hemispherical detector without the jaw portion detector. As illustrated in FIG. 2, the helmet-type PET device of a radius R=125 mm (A), a cylindrical PET device of the radius R=125 mm and a length L=125 mm (B), and an open-type PET device (Open PET) of the radius R=125 mm, a length W of a detector ring=62.5 mm, and a length G of an open space=62.5 mm (C), which were prepared for measurement of a head of a human, were compared in sensitivity distribution. Here, the three compared geometries are all have the same detector surface area; and therefore an amount of detector for configuring the device is almost uniform. As illustrated in FIG. 2, although the PET devices have the same amount of detector, the helmet-type PET device (A), which is constituted according to the shape of visual field, entirely features high sensitivity. Especially, it is seen that the margin portion, namely, the portion where a cerebrum is positioned, features considerably high sensitivity compared with the hemispherical FOV required for measurement of the head. On the other hand, the cylindrical PET device (B) also opens the parietal region. This deteriorates the sensitivity. Accordingly, for measurement of the brain functions, it is necessary that the length of the cylinder be lengthen so as to widen a high sensitivity region. This tremendously increases the amount of the detector. On the other hand, in the case where the Open PET (C), because of the open space between the detector rings, the FOV is expanded. The sensitivity of the Open PET becomes the highest at the center of the open space. Accordingly, the part corresponding to the margin portion at the helmet-type PET device becomes high sensitivity with the Open PET; however, the helmet-type PET device features higher sensitivity—almost double.

A weak point of the helmet-type PET device constituted only with the hemispherical detector 20 is low sensitivity at the center portion compared with other parts. Therefore, the present invention proposes a method for disposing a detector at a jaw part to compensate the low sensitivity portion. The method for determining the size of the jaw portion detector 30 is as follows. First, the jaw portion detector 30 is defined on a sphere the same as the hemispherical detector 20. Then, as illustrated in FIG. 3 (side view and front view), the open angle parameter $\alpha$, which determines the width in the horizontal direction, and the open angle parameter $\beta$, which determines the width in the vertical direction, are defined.

Figure 4:
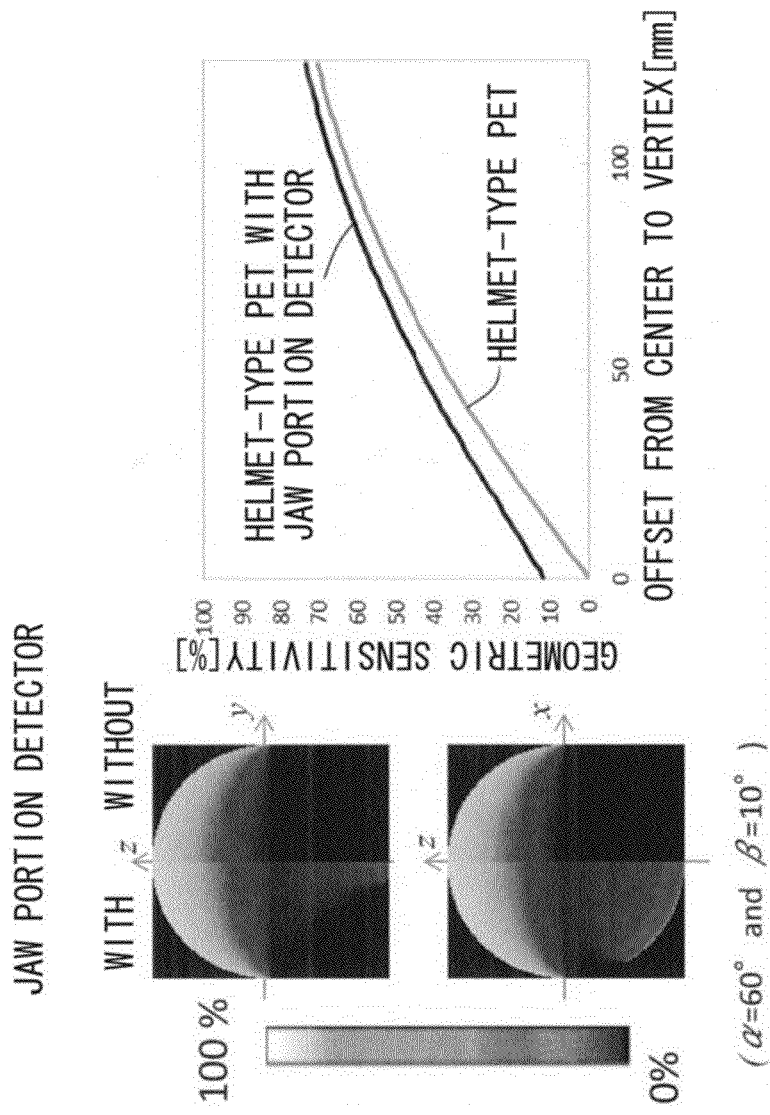
FIG. 4 similarly illustrates a change in the sensitivity at the reference regions accompanied by an increase of the jaw portion detectors.

To show effectivity of the jaw portion detector 30, results of comparison of sensitivity distributions on a straight line from the center to the parietal region between the PET device without the jaw portion detector and the PET device with the jaw portion detector 30 of $\alpha=60°$ and $\beta=10°$ are illustrated in FIG. 4. The sensitivity distribution is laterally symmetrical; therefore, for ease of the comparison, the sensitivity distributions of the case with the jaw portion detector are shown on the left half and the sensitivity distributions of the case without the jaw portion detector are shown on the right half. It is seen that in the case where only the hemispherical detector 20 is used, the position at which the sensitivity is low can be efficiently improved.

Figure 3:
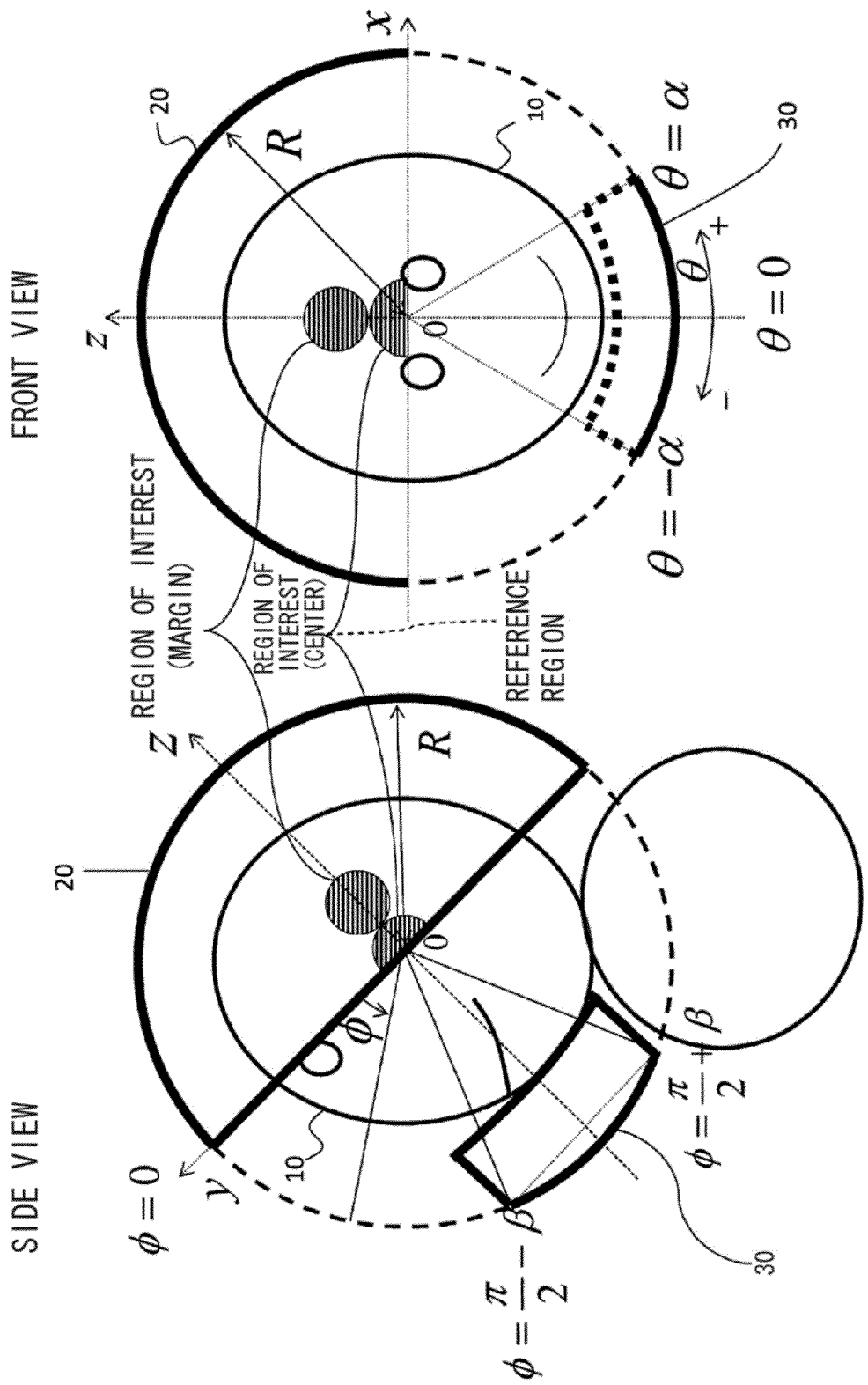
FIG. 3 illustrates parameters defining a size of a jaw portion detector according to a first embodiment and reference regions for comparison of sensitivity.
Figure 5A:
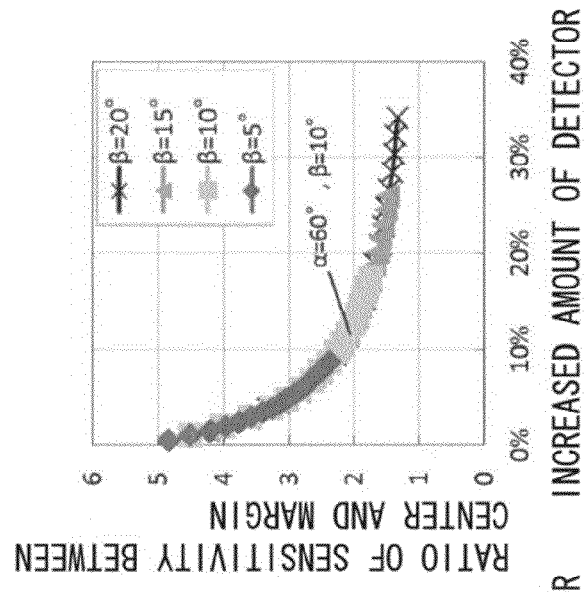
FIGS. 5A to 5C similarly illustrate the change in sensitivity distribution when the jaw portion detector is added to the hemispherical detector.
Figure 5B:
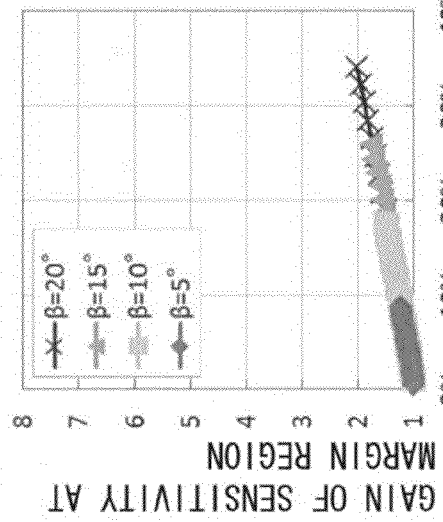
Figure 5C:
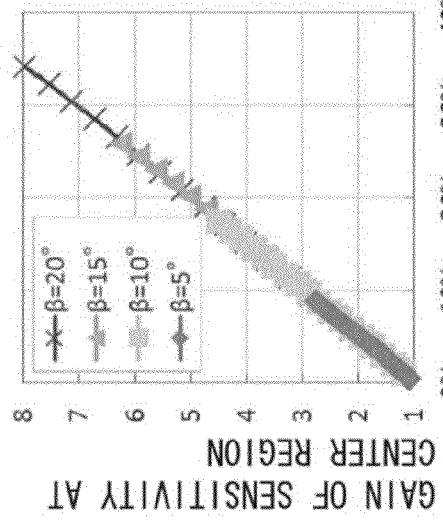

To examine the change in sensitivity when the size of the jaw portion detector 30 is changed by changing $\alpha$ and $\beta$, as illustrated in FIG. 3, regions of interest (ROI) are set at the margin and the center and an average sensitivity of these regions is obtained. FIGS. 5A to 5C illustrate the change in sensitivity of the reference regions accompanied by the increase of the jaw portion detector 30. Compared with the case where the jaw portion detector 30 is absent, gains of the center region and the margin region that indicate to what extent the sensitivity is amplified accompanied by the increased amount of the detector are shown. The increased amount of the detector is defined as the surface area of the jaw portion detector 30 with respect to the surface area of the hemispherical detector 20. Additionally, to indicate the difference in sensitivity between the center region and the margin region, a sensitivity ratio with respect to the increased amount of the detector is shown. The gain of the sensitivity is set as a ratio of the sensitivity with respect to the case where the jaw portion detector is absent. The following can be observed. Even if the jaw portion detector 30 is increased, the sensitivity at the margin region does not change so much while the sensitivity at the center region is significantly improved. As a result of plotting the sensitivity ratios at the center and the margin, the following is shown. Only increasing the amount of the detector by around 12% improves the difference in sensitivity of the hemispherical detector 20 alone, which is originally around five times, is improved to around twice. The size of the jaw portion detector 30 at this time is $\alpha=60°$ and $\beta=10°$.

Figure 6:
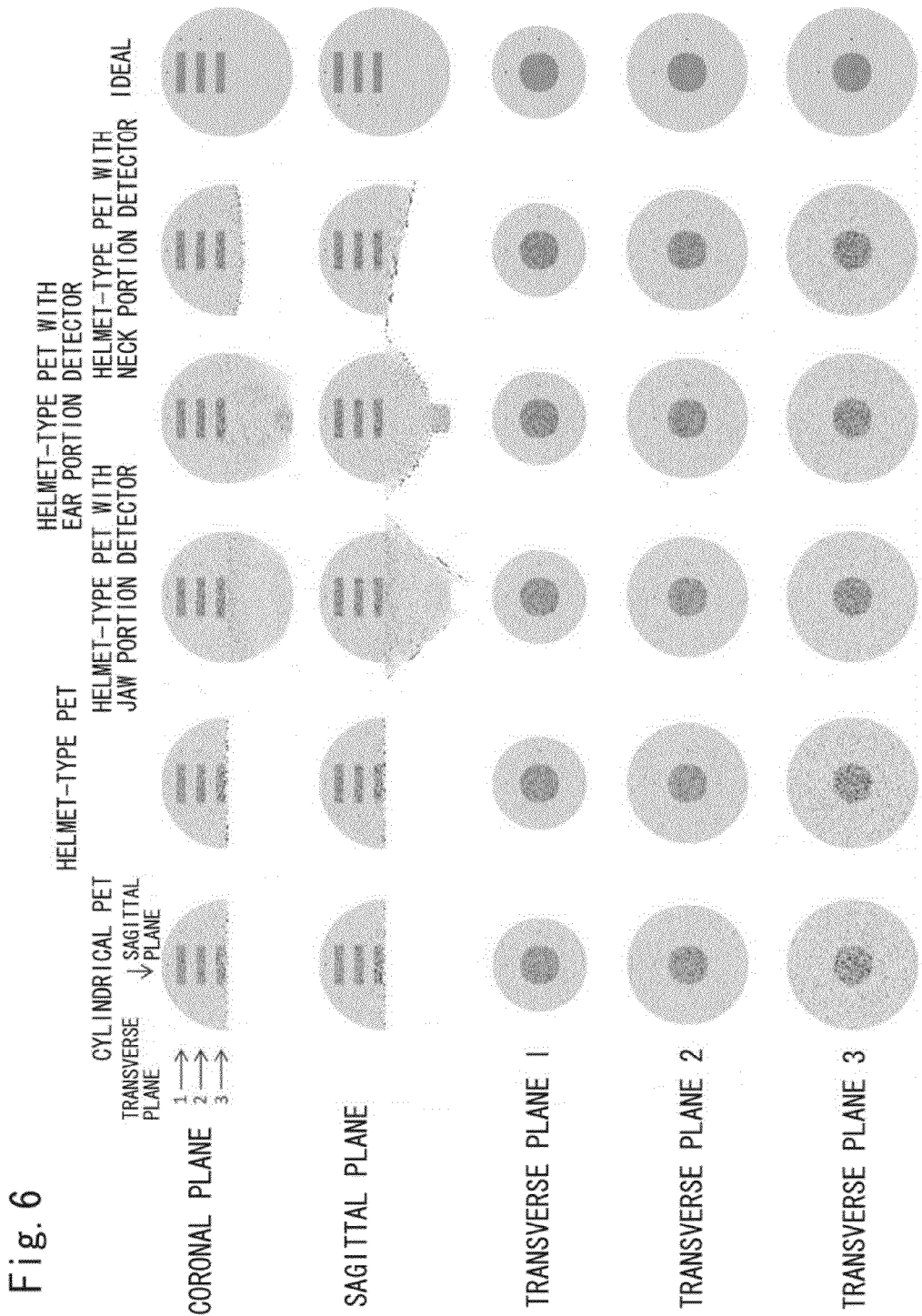
FIG. 6 are drawings for comparisons of imaging performance where projection data of respective geometries of the cylindrical PET device, the helmet-type PET device, a helmet-type PET device with the jaw portion detector, a helmet-type PET device with an ear portion detector, and a helmet-type PET device with a neck portion detector are obtained, statistical noise is given to the projection data, and three-dimensional image reconstruction is performed on the projection data by computer simulation.
Figure 7:
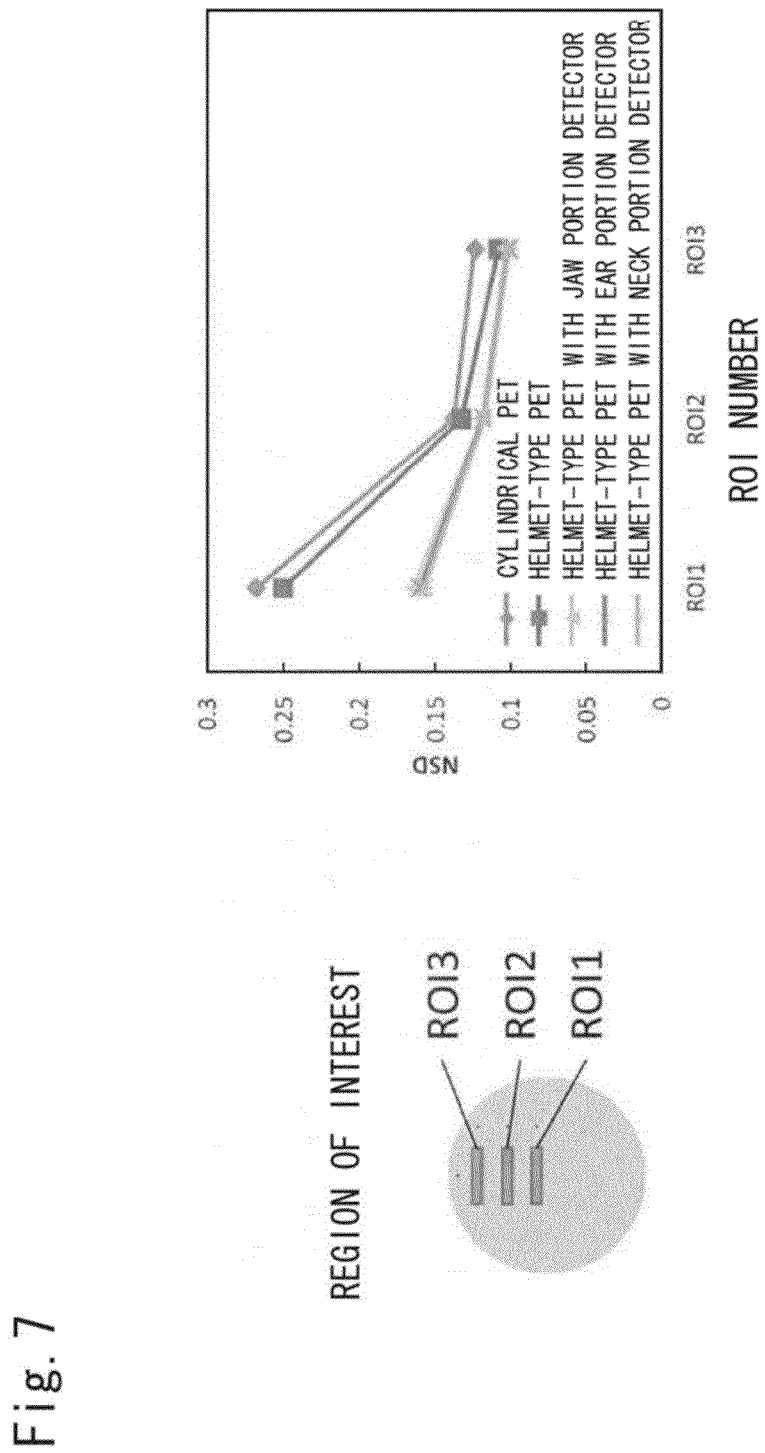
FIG. 7 is a drawing where regions of interests were set in respective disks and a normalized standard deviation, which is a value dividing a value of standard deviation into an average value, was obtained to quantitatively evaluate the images in FIG. 6.
Figure 18:
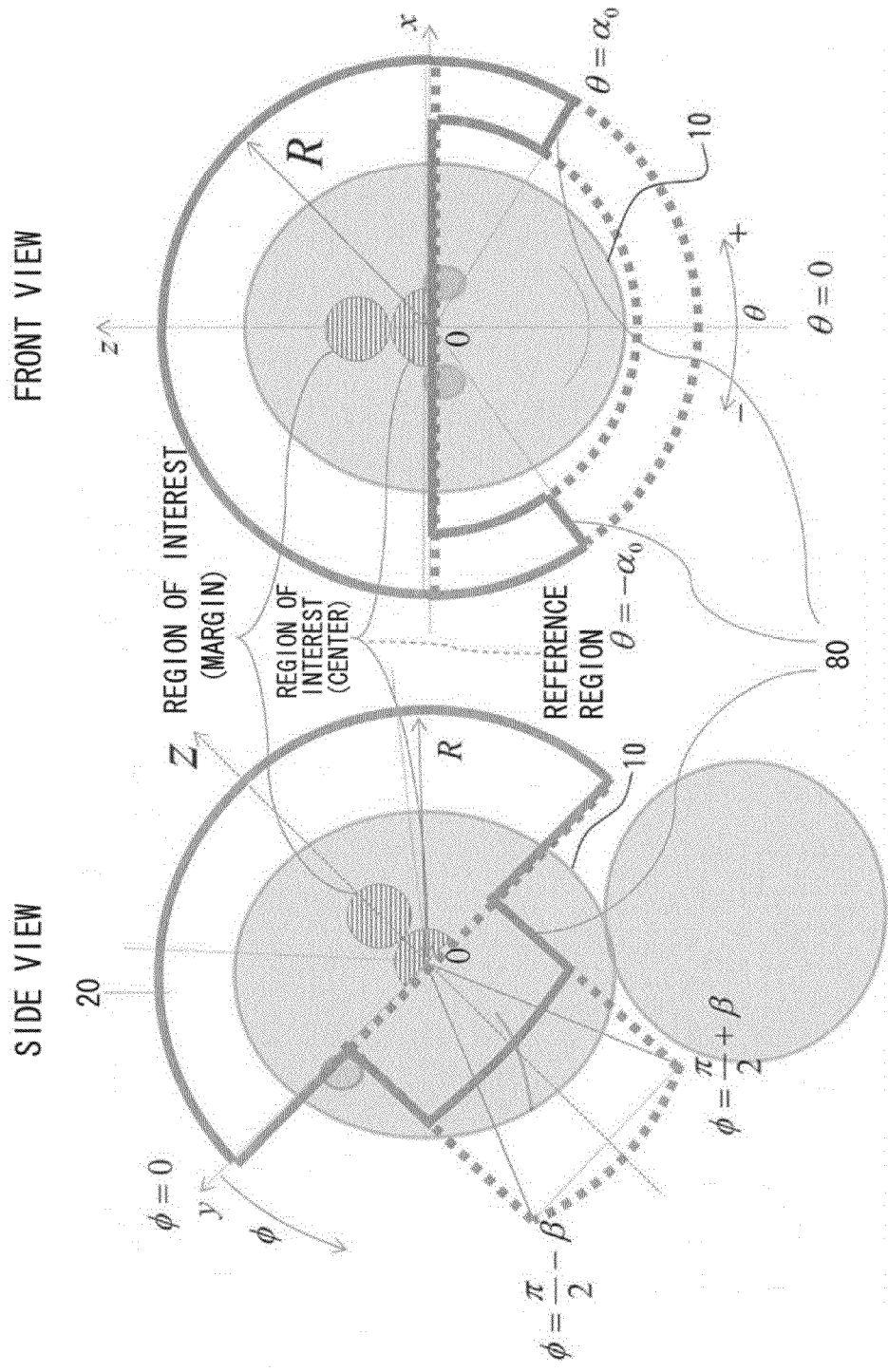
FIG. 18 is a conceptual diagrams of the second embodiment of the present invention.
Figure 19:
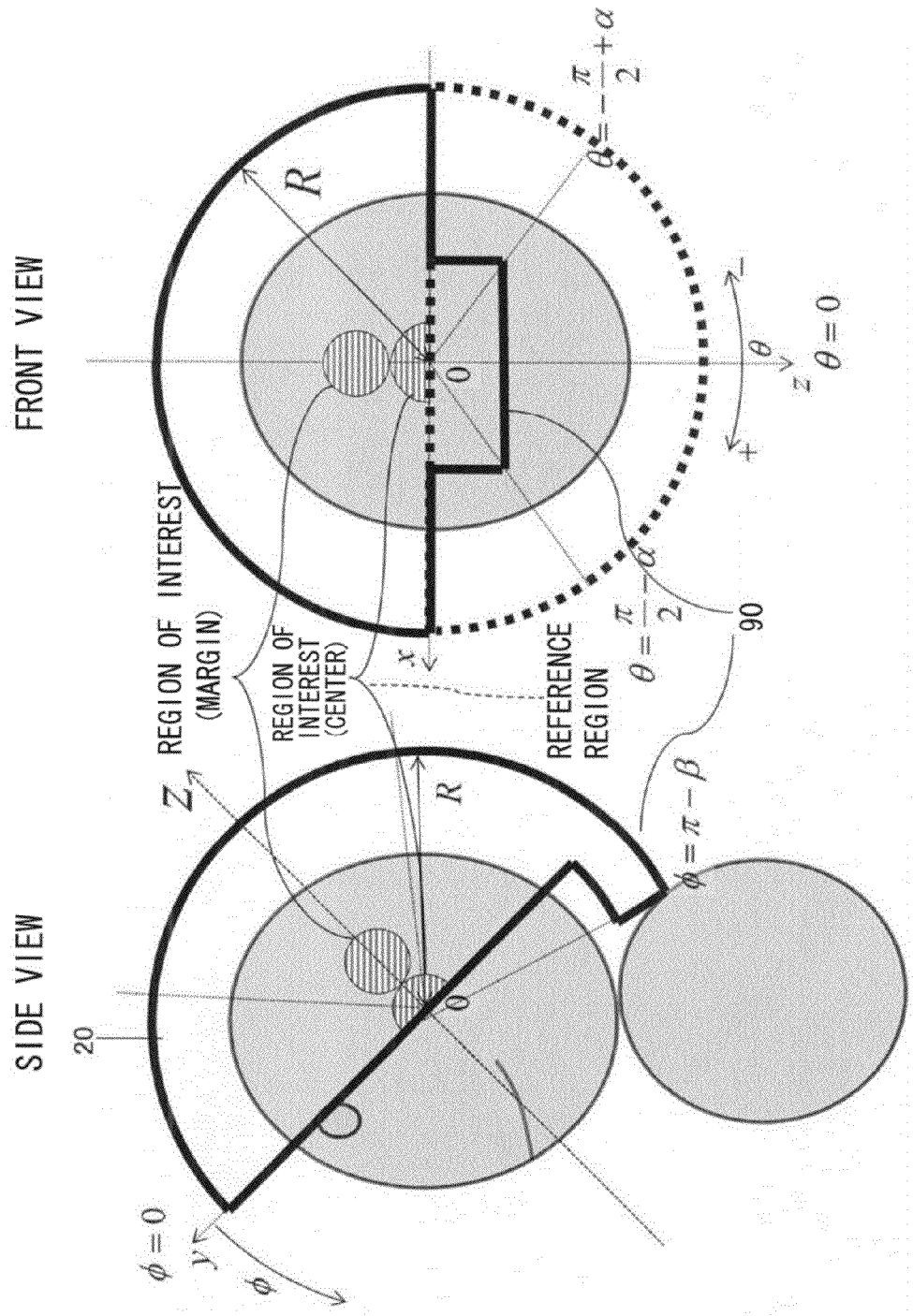
FIG. 19 is a conceptual diagrams of the third embodiment of the present invention.

FIG. 6 and FIG. 7 illustrate results of computer simulation for evaluation of imaging performance. For comparison of the imaging performance, projection data of respective geometries of the cylindrical PET device, the helmet-type PET device, the helmet-type PET device with the jaw portion detector of the first embodiment, a helmet-type PET device with an ear portion detector of a second embodiment to which an ear portion detector 80 illustrated in FIGS. 18A and 18B, which will be described later, is added, and a helmet-type PET device with a neck portion detector of a third embodiment to which a neck portion detector 90 illustrated in FIGS. 19A and 19B, which will be described later, is added, were obtained, statistical noise was given to the projection data, and three-dimensional image reconstruction was performed on the projection data by computer simulation. The size of the jaw portion detector 30 of the helmet-type PET device with the jaw portion detector was set to α=60° and β=10°. The size of the respective scintillators was assumed to be 3 mm square-sized. As numerical phantoms, three disks and six point-shaped accumulations were defined in a spherical background. Setting the total number of generated gamma ray pair as 500 M counts, the number of counts of the projection data was determined by a product of the total number of generated gamma ray pair and the geometric sensitivity in the geometry of each device. The coronal plane and sagittal plane indicate cross sections passing through the center and as transverse planes, cross sections with the disks and the point-shaped accumulations are illustrated. In particular, the cross section closer to the center exhibited remarkable effect of the jaw portion detector 30, providing better image quality.

To evaluate the noise quantitatively, the region of interests were set in the respective disks, and a normalized standard deviation, which is a value dividing a value of standard deviation into an average value, was obtained. The left drawing in FIG. 7 illustrates the positions of the regions of interest, ROI1, ROI2, and ROI3. With the cylindrical PET device and the helmet-type PET device alone, noise becomes considerably large at the position close to the center of the sphere. In contrast to this, with the helmet-type PET device with the jaw portion detector of the first embodiment to which the jaw portion detector 30 is added, the helmet-type PET device with an ear portion (a lateral side) detector of the second embodiment to which the ear portion detector 80 is added, and the helmet-type PET device with a neck portion (a lower side) detector of the third embodiment to which the neck portion detector 90 is added, the noise can be substantially reduced.

Here, normalized standard deviation (NSD), which is a parameter indicative of image quality, is expressed by the following expression.

$$NSD_n = \frac{\sqrt{\frac{1}{N}\sum_{j \in ROI_n}(f_j - \hat{f}_n)^2}}{\hat{f}_n} \quad \text{[Expression 1]}$$

$$\hat{f}_n = \frac{1}{N}\sum_{j \in ROI_n} f_j, \quad N = \sum_{j \in ROI_n} 1$$

Figure 8:
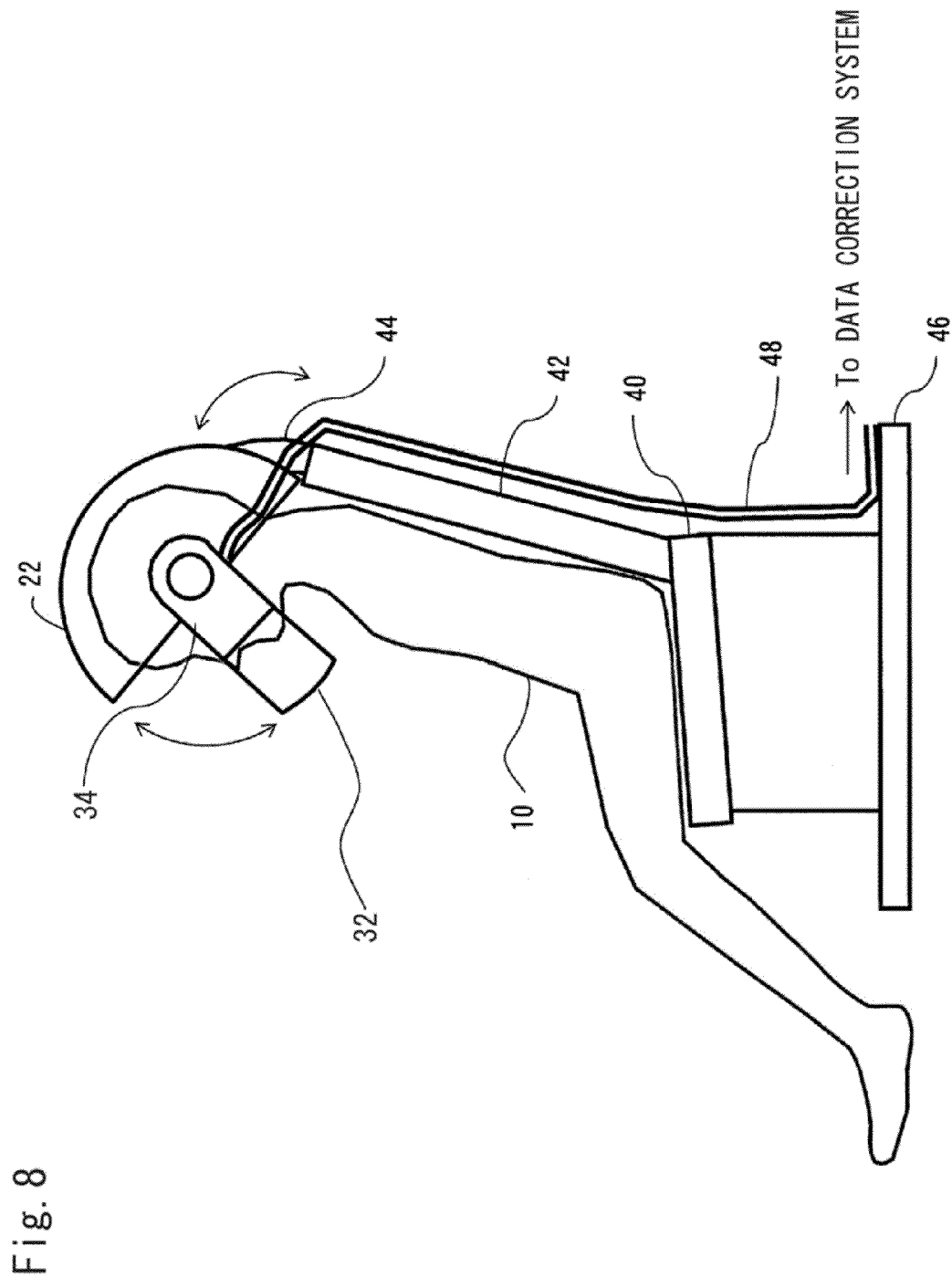
FIG. 8 illustrates a method for mounting and a posture during measurement according to the first working example to achieve the helmet-type PET device with the jaw portion detector.

FIG. 8 illustrates the first working example for achieving the helmet-type PET device with the jaw portion detector. Integrating the helmet-type PET device with a chair 40 allows reducing a burden to an examination target (examinee) 10 during the measurement. A gantry 22 of the hemispherical is configured to be movable. The jaw portion detector 30 includes a gantry 32. The gantry 32 includes a joint portion 34 for mounting the hemispherical detector gantry 22. This allows facilitating removal/mounting.

In the diagram, reference numeral 42 denotes a backrest, reference numeral 44 denotes a support pillar of the hemispherical detector gantry 22, reference numeral 46 denotes a pedestal, and reference numeral 48 denotes a data signal line.

Figure 9:
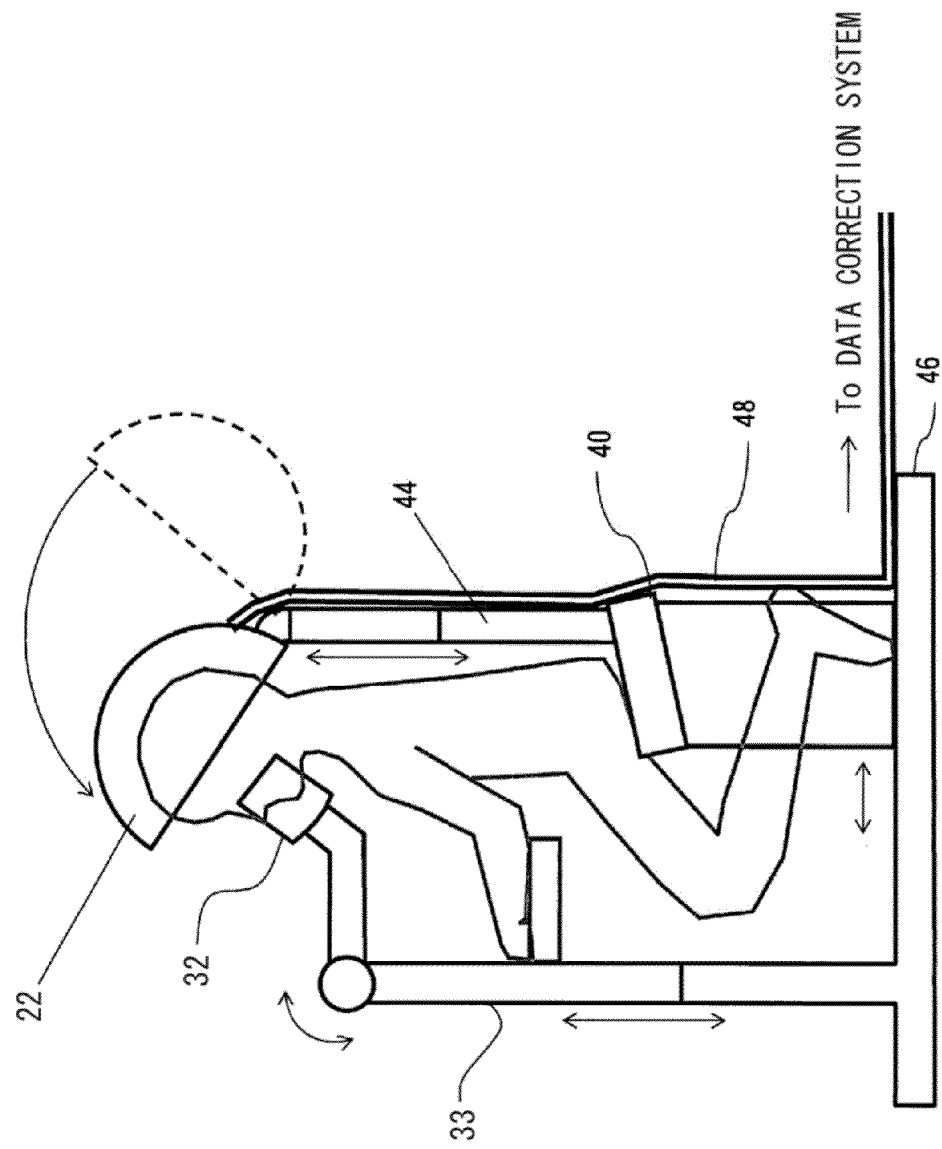
FIG. 9 similarly illustrates a method for mounting and a posture during measurement according to a second working example.

FIG. 9 similarly illustrates a second working example for achieving the helmet-type PET device with the jaw portion detector. This working example differs from the first working example in that the chin rest and jaw portion detector gantry 32 is supported by a support pillar 33 so as to double as a chin rest. The other points are substantially the same as in the first working example and therefore the description is omitted.

Figure 10:
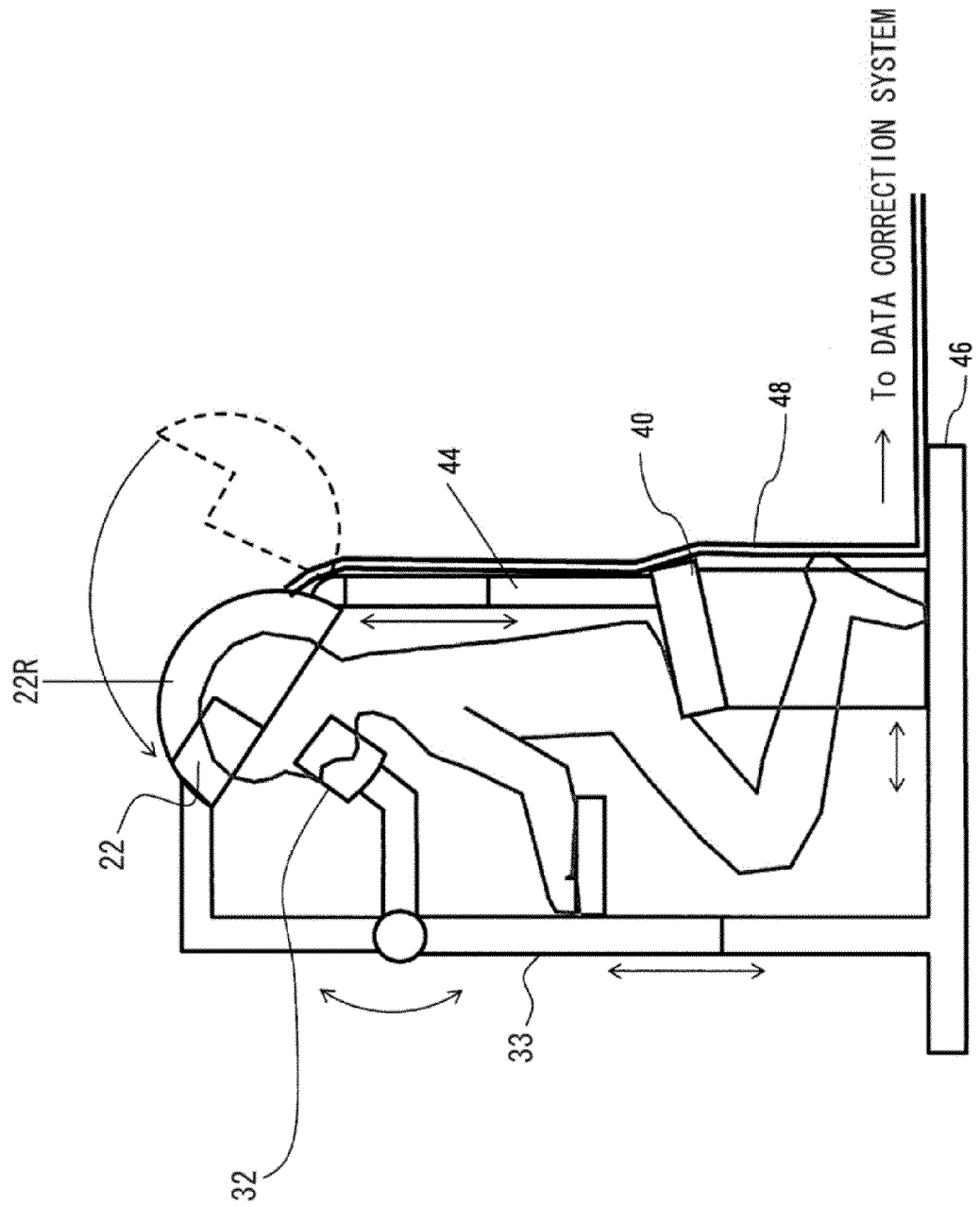
FIG. 10 similarly illustrates a method for mounting and a posture during measurement according to a third working example.

FIG. 10 similarly illustrates a third working example for achieving the helmet-type PET device with the jaw portion detector. This working example differs from the second working example in the following points. The hemispherical detector gantry 22 is divided into a front portion 22F and a rear portion 22R. The front portion 22F is supported by the support pillar 33 together with the chin rest and jaw portion detector gantry 32. The other points are substantially the same as in the second working example and therefore the description is omitted.

Figure 11:
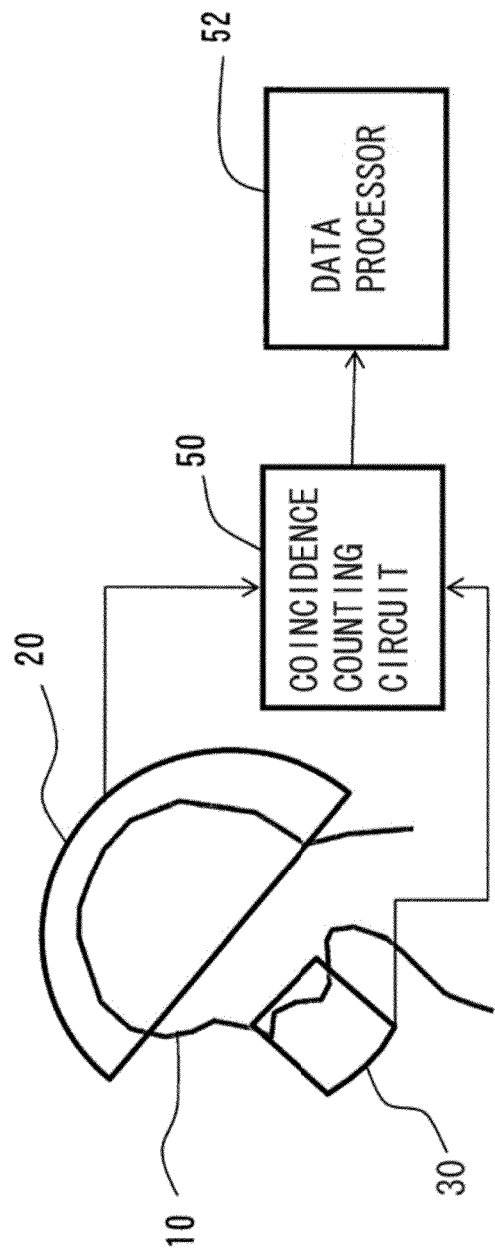
FIG. 11 is a block diagram illustrating a signal processing system of the first embodiment.

As illustrated in FIG. 11, signals from the hemispherical detector 20 and the jaw portion detector 30 are sent to a coincidence counting circuit 50. After coincidence counting determination is performed, the signals are sent to a data processor 52 as coincidence counting data. The coincidence counting determination is performed between the scintillators in the hemispherical detector 20 and also between the scintillator of the hemispherical detector 20 and that of the jaw portion detector 30.

Figure 12:
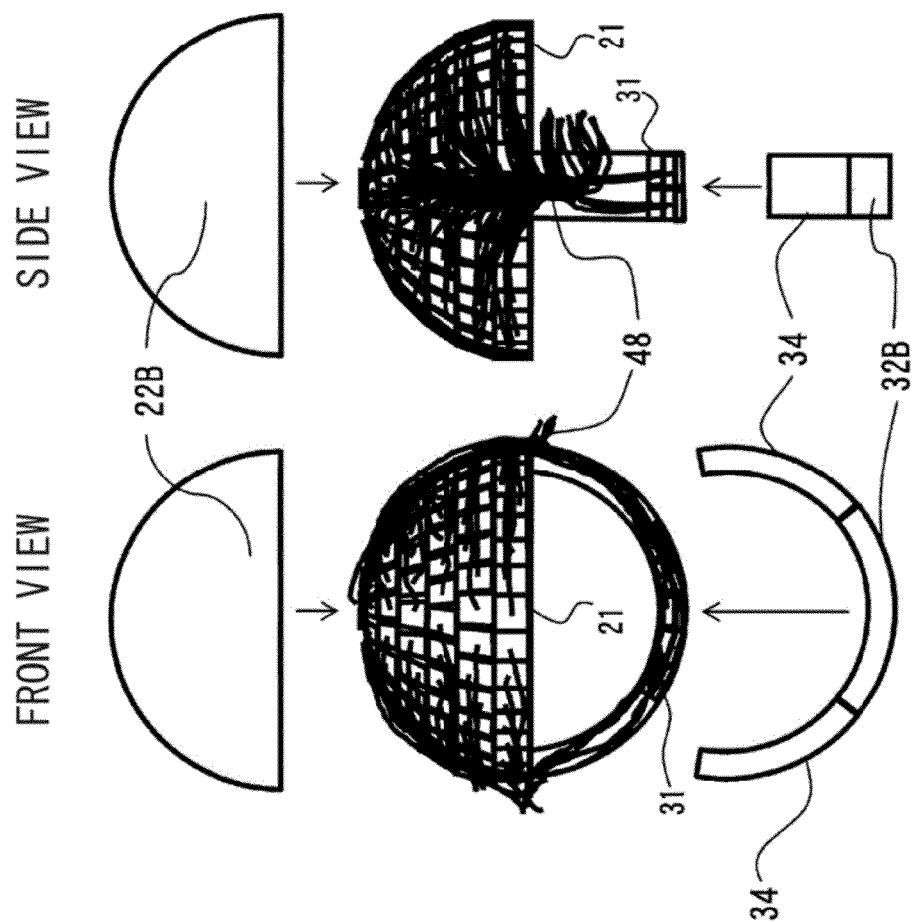
FIG. 12 is a front view and a side view, similarly illustrating a method for securing a detector to an outer gantry.
Figure 13B:
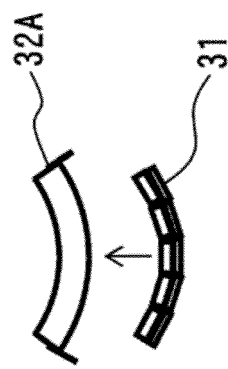
FIG. 13A similarly illustrates a method for securing the detector to the hemispherical detector, and FIG. 13B similarly illustrates a method for securing the detector to an inner gantry of the jaw portion detector.
Figure 13A:
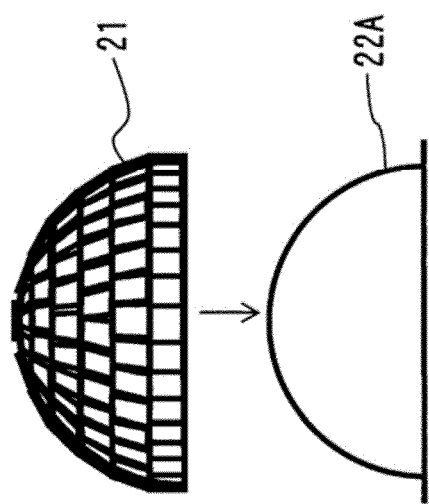

FIG. 12 and FIGS. 13A and 13B illustrate a method for securing the detector to the inside of the gantry. After mounting the data signal lines 48 to the respective elements, a PET detector 21, which constitutes the hemispherical detector 20, is secured to the inside of hemispherical detector gantries 22A (see FIG. 13A) and 22B (see FIG. 12) divided into the inside and outside. Similarly, a PET detector 31, which constitutes the jaw portion detector 30, is secured to inner portions 32A of jaw portion detector gantries (see FIG. 13B) and 32B (see FIG. 12) divided into the inside and outside. The PET detector 31 is mounted to the hemispherical detector gantry 22 with a joint part 34.

FIGS. 14A to 14G list available configurations of the PET detectors. FIG. 14A illustrates a block-type detector that includes a photodetector 62 at one side (lower side in the drawing) of a scintillator array 60. FIG. 14B illustrates a monolithic block-type detector that includes the photodetector 62 at one side (lower side in the drawing) of a monolithic scintillator 64. FIG. 14C illustrates a pixel-type curved surface detector that includes the photodetectors 62 at one side (lower side in the drawing) of a curved surface scintillator array 66. FIG. 14D illustrates a detector that includes scintillators 68 and the photodetectors 62 coupled on a one-on-one basis. FIG. 14E illustrates a double-sided reading block-type detector that includes the photodetectors 62 arrayed at both sides (upper and lower sides in the drawing) of the scintillator array 60. FIG. 14F illustrates a monolithic-curved-surface-type detector that includes the photodetectors 62 at one side (lower side in the drawing) of a curved surface monolithic scintillator 70. FIG. 14G illustrates a triangular-shaped photodetector (hereinafter referred to as a triangular-patch-type detector) that includes triangular-patch-type detectors 74 at one side (lower side in the drawing) of a triangular pole scintillator array 72.

FIG. 15A illustrates an exemplary cross section of an arrangement method for the block-type detectors. FIG. 15B illustrates an exemplary cross section of an arrangement method for the curved surface detectors. FIG. 15C illustrates an example of an arrangement method of the photodetectors 62 with a quadrangular bottom surface to a spherical surface. FIG. 15D illustrates an example of an arrangement method of the triangular-patch-type detectors 74 to the spherical surface. As illustrated in FIG. 15D, if the bottom surfaces of the triangular-patch-type detectors 74 have a triangular shape, the triangular-patch-type detectors 74 can be gaplessly disposed in an almost hemispherical shape. However, as illustrated in FIG. 15C, even if the detectors with the quadrangular bottom surface are used, the detectors can be disposed at sufficient density insofar as the size of the detectors is small, 1 to 3 mm square-sized.

FIG. 16C illustrates an exemplary arrangement of soccer-ball-shaped detectors formed with hexagonal detectors 76 (FIG. 16A) and pentagonal detectors 78 (FIG. 16B).

FIGS. 17A and 17B illustrate exemplary configurations of the hexagonal detectors 76 and the pentagonal detectors 78 arranged in a triangular pole scintillator array 72, respectively. The hexagonal detector 76 illustrated in FIG. 17A is formed by a regular triangle, and the pentagonal detector 78 illustrated in FIG. 17B is formed by an isosceles triangle whose apex angle is 72°.

Figure 20:
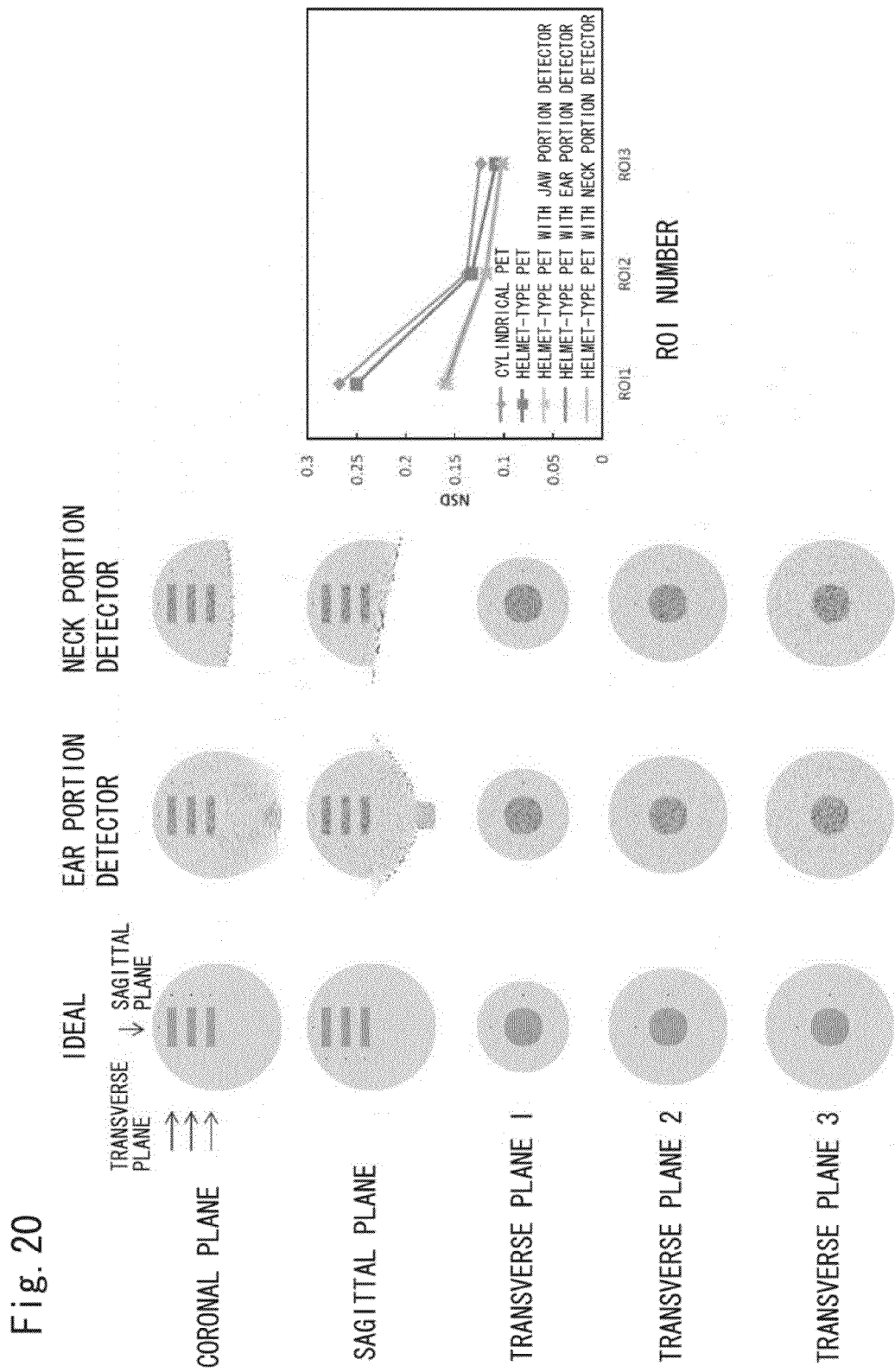
FIG. 20 is a drawing where three-dimensional reconstructions are performed in the second and the third embodiments of the present invention.

Note that a detector to be added is not necessarily to be at the jaw portion. As the second embodiment illustrated in FIG. 18, for example, the ear portion detector 80 is disposed at an ear position. As the third embodiment illustrated in FIG. 19, a rear of the hemispherical detector 20 is extended to form the neck portion detector 90 or to be disposed at a cheek part. These arrangements achieve improvement of the sensitivity at the center portion. Examples where the three-dimensional reconstructions were performed in the second and third embodiments are illustrated in FIG. 20. The analytically calculated surface areas of the ear portion detector method and the neck portion detector method by extending an occipital region were the same as the analytically calculated surface area of the jaw portion detector method. The NSD values of the reconstruction images were almost the same in each add-on method. The reason of generating slight difference seemed that in the case where the detectors were configured with separate detector elements whose bottom surface was assumed to be 3 mm×3 mm, it makes a slight difference in the respective methods.

The numbers of elements were 10668 when only the hemispherical detector was employed, 11880 by the jaw portion detector method, 11884 by the ear portion detector method, and 11887 by the neck detector method by extending the occipital region.

In the embodiment, since all the PET detectors were disposed on the same spherical surface, this makes the calculation simple. As in forth embodiment shown in FIGS. 21A to 21C, disposing the PET detectors 26, 38 close on a non-spherical surface according to the shape of the head and/or jaw of the examination target 10 downsizes the device. This allows reducing the number of PET detectors and the cost reduction, also allowing enhancing the sensitivity.

INDUSTRIAL APPLICABILITY

The brain PET is effective for early diagnosis of a disease, such as the Alzheimer's disease and the Parkinson's disease, and investigation of nervous activity.

What is claimed is:

1. A helmet-type brain PET device, comprising:
a helmet portion that includes a PET detector; and
an added portion positioned to dispose a PET detector at a part other than the helmet portion, wherein
PET measurement is performed using both an output from the PET detector at the helmet portion and an output from the PET detector at the added portion.

2. The helmet-type PET device according to claim 1, wherein
the added portion is positioned at a front side, at least one lateral side, or a lower side of the helmet portion.

3. The helmet-type PET device according to claim 1, wherein
the PET detector at the helmet portion and the PET detector at the added portion are disposed on a same spherical surface.

4. The helmet-type PET device according to claim 1, wherein
the PET detector at the helmet portion and the PET detector at the added portion are disposed close to a head of the examination target according to a shape of the examination target.

5. The helmet-type PET device according to claim 1, wherein
the helmet portion has a shape of a hemisphere.

6. The helmet-type PET device according to claim 2, wherein
the added portion is positioned at the front side of the helmet portion with an open angle α in horizontal direction more than 0.5 degree and less than 90 degree, preferably 60 degree, and an open angle β in vertical direction more than 0.5 degree and less than 40 degree, preferably 10 degree.

7. The helmet-type PET device according to claim 1, wherein
detector elements consisting the PET detector has a size less than about 3 mm square.

8. The helmet-type PET device according to claim 1, wherein
the helmet portion and the added portion are integrated into a chair.

9. The helmet-type PET device according to claim 1, wherein
the added portion is disposed on a chin rest.

10. The helmet-type PET device according to claim 9, wherein
the helmet portion is divided into a front portion and a rear portion, and the front portion is supported by a pillar together with the chin rest.

11. The helmet-type PET device according to claim 1, wherein
the PET detector is one of a block-type detector, a monolithic block-type detector, a pixel-type curved surface detector, one-to-one basis coupling-type detector, a double-sided reading block-type detector, a monolithic-curved-surface-type detector and a triangular-patch-type detector.

12. The helmet-type PET device according to claim 1, wherein
the PET detector is constituted by hexagonal detectors and pentagonal detectors, which are arranged into a soccer ball shape.

13. The helmet-type PET device according to claim 12, wherein
the hexagonal detectors are constituted by arranging triangular pole scintillators having a cross section of regular triangle, and the pentagonal detectors are constituted by arranging triangular pole scintillators having a cross section of isosceles triangle.

* * * * *